United States Patent
Bonel et al.

(10) Patent No.: US 10,544,658 B2
(45) Date of Patent: Jan. 28, 2020

(54) UNDERWATER CONTROL DEVICE AND CONTROL SYSTEM FOR AN UNDERWATER HYDROCARBON PRODUCTION FACILITY

(71) Applicant: SAIPEM S.p.A., San Donato Milanese (IT)

(72) Inventors: Paolo Bonel, Venice (IT); Alfredo Rotella, San Donato Milanese (IT); Roberto Visentin, Mestre (IT)

(73) Assignee: SAIPEM S.p.A., San Donato Milanese (IT)

(*) Notice: Subject to any disclaimer, the term of this patent is extended or adjusted under 35 U.S.C. 154(b) by 0 days.

(21) Appl. No.: 16/069,284

(22) PCT Filed: Jan. 13, 2017

(86) PCT No.: PCT/IB2017/050194
§ 371 (c)(1),
(2) Date: Jul. 11, 2018

(87) PCT Pub. No.: WO2017/122172
PCT Pub. Date: Jul. 20, 2017

(65) Prior Publication Data
US 2019/0032453 A1    Jan. 31, 2019

(30) Foreign Application Priority Data

Jan. 14, 2016 (IT) .................. 102016000003084

(51) Int. Cl.
*E21B 41/00* (2006.01)
*G01N 33/18* (2006.01)
(Continued)

(52) U.S. Cl.
CPC ......... *E21B 41/0007* (2013.01); *G01N 33/18* (2013.01); *H05K 5/0017* (2013.01);
(Continued)

(58) Field of Classification Search
None
See application file for complete search history.

(56) References Cited

U.S. PATENT DOCUMENTS

| | | | | |
|---|---|---|---|---|
| 4,291,932 A | * | 9/1981 | Cox | H01R 13/523 439/271 |
| 7,849,704 B2 | * | 12/2010 | Ashibe | H01R 4/68 62/259.2 |

(Continued)

FOREIGN PATENT DOCUMENTS

| | | |
|---|---|---|
| EP | 2 487 326 A1 | 8/2012 |
| EP | 2 666 956 A1 | 11/2013 |

(Continued)

OTHER PUBLICATIONS

Notification Concerning Submission, Obtention or Transmittal of Priority Document for International Application No. PCT/IB2017/050194 dated Apr. 21, 2017.

(Continued)

*Primary Examiner* — Xanthia C Cunningham
(74) *Attorney, Agent, or Firm* — Neal, Gerber & Eisenberg LLP

(57) ABSTRACT

An underwater control device for an underwater hydrocarbon production facility having an underwater box defining a housing chamber; an active electronic component with a switching and/or isolation function, housed in the housing chamber; a polymer block in which the active electronic component is embedded, and which is housed in the housing chamber; and electrical connectors extending through the underwater box and configured to connect the active electronic component to a network of a control system.

16 Claims, 4 Drawing Sheets

(51) Int. Cl.
  *H05K 5/00* (2006.01)
  *H05K 5/02* (2006.01)
  *H05K 5/06* (2006.01)
  *H01R 13/523* (2006.01)

(52) U.S. Cl.
  CPC ......... *H05K 5/0056* (2013.01); *H05K 5/0247* (2013.01); *H05K 5/069* (2013.01); *H01R 13/523* (2013.01)

(56) References Cited

U.S. PATENT DOCUMENTS

| | | | | |
|---|---|---|---|---|
| 8,381,578 | B2* | 2/2013 | Sweeney | B63C 11/42 405/154.1 |
| 8,439,080 | B2* | 5/2013 | Uusipaikka | E21B 33/0385 138/26 |
| 8,444,283 | B1* | 5/2013 | Miller | F21V 15/01 362/101 |
| 9,035,739 | B2* | 5/2015 | Boe | H01H 85/0021 337/186 |
| 2004/0097131 | A1* | 5/2004 | Varreng | H01R 13/523 439/587 |
| 2008/0309346 | A1* | 12/2008 | MacGregor | G01V 3/083 324/334 |
| 2009/0078028 | A1* | 3/2009 | McStay | E21B 43/0122 73/45.5 |
| 2011/0305115 | A1* | 12/2011 | Jiang | G01K 1/024 367/141 |
| 2012/0255706 | A1* | 10/2012 | Tadayon | F28D 20/0039 165/47 |
| 2014/0103224 | A1* | 4/2014 | Ng | G01N 21/05 250/435 |
| 2014/0211589 | A1* | 7/2014 | Maxwell | G01V 1/18 367/15 |
| 2014/0312713 | A1* | 10/2014 | Wentzler | H01H 35/32 307/118 |
| 2015/0000582 | A1* | 1/2015 | Lelaurin | G01V 1/3852 114/257 |
| 2015/0138920 | A1* | 5/2015 | Hiller | H04B 11/00 367/87 |
| 2015/0346726 | A1* | 12/2015 | Davoodi | B63B 22/24 701/21 |
| 2016/0041280 | A1* | 2/2016 | Naes | G01V 1/18 367/149 |
| 2016/0057880 | A1* | 2/2016 | Hanke | A01K 63/06 361/752 |
| 2016/0259073 | A1* | 9/2016 | Tenghamn | G01V 1/143 |
| 2017/0059441 | A1* | 3/2017 | Latini | G01M 3/002 |
| 2018/0321385 | A1* | 11/2018 | Embry | G01S 17/89 |
| 2018/0337737 | A1* | 11/2018 | Hyland | H04B 13/00 |
| 2018/0364385 | A1* | 12/2018 | Woodward | B63C 11/52 |
| 2019/0081435 | A1* | 3/2019 | Lewin | H01R 13/523 |

FOREIGN PATENT DOCUMENTS

| | | | | |
|---|---|---|---|---|
| EP | | 2666956 A1 * | 11/2013 | ........... E21B 33/037 |
| WO | WO 2007/010179 | A1 | 1/2007 | |
| WO | WO 2015/188882 | A1 | 12/2015 | |
| WO | WO-2015188882 | A1 * | 12/2015 | ......... E21B 33/0355 |

OTHER PUBLICATIONS

International Search Report and Written Opinion for International Application No. PCT/IB2017/050194 dated May 11, 2017.
PCT Demand for International Preliminary Examination and Reply to International Search Report and the associated Written Opinion for International Application No. PCT/IB2017/050194 dated Nov. 13, 2017.
Communication from the International Preliminary Examining Authority for International Application No. PCT/IB2017/050194 dated Jan. 4, 2018.
Notification of Transmittal of the International Preliminary Report on Patentability (Form PCT/IPEA/416) for International Application No. International Application No. PCT/IB2017/050194 dated Jan. 19, 2018.
Offshore Technology Conference 24307 presentation "Steps to Subsea Factory" by O. Oekland et al, Oct. 29, 2013 (10 pages).

* cited by examiner

UNDERWATER CONTROL DEVICE AND CONTROL SYSTEM FOR AN UNDERWATER HYDROCARBON PRODUCTION FACILITY

PRIORITY CLAIM

This application is a national stage application of PCT/IB2017/050194, filed on Jan. 13, 2017, which claims the benefit of and priority to Italian Patent Application No. 102016000003084, filed on Jan. 14, 2016, the entire contents of which are each incorporated by reference herein.

TECHNICAL FIELD

The present disclosure relates to a control device for an underwater hydrocarbon production facility.

In particular, the present disclosure relates to an underwater control device of a control system configured to control an underwater hydrocarbon production facility. In the description that follows, the term "hydrocarbon production" means both the processing of hydrocarbons and the processing of fluids related to hydrocarbon production.

BACKGROUND

Underwater hydrocarbon production facilities can be placed relatively close to subsea wells or in relatively intermediate locations, and can have various configurations on the bed of a body of water, depending on the hydrocarbon well or well field. In addition, underwater hydrocarbon production facilities can be positioned in relatively shallow water or in relatively very deep water and in any geographic area, independently of whether environmental conditions are relatively mild or relatively extreme.

The concept of an underwater hydrocarbon production facility was developed by operators in the industry with the objective of rationalizing hydrocarbon production from subsea wells. In short, an underwater hydrocarbon production facility is part of a complex installation that comprises an underwater hydrocarbon production facility and pipelines for long-distance transportation between underwater facilities and surface structures. The exploitation of subsea oil and/or gas fields via underwater hydrocarbon production facilities that provide for the extraction and transport of the hydrocarbon to the surface or coast has been under way for some time and expansion in the near future is foreseeable. Recent technological developments in underwater devices suitable for working at relatively great depths and the interest of oil companies have facilitated the feasibility of complex systems, broadened the potentiality of underwater production facilities and made any type of active process in water possible. The main underwater treatment processes are: fluid pumping or compression; multiphase pumping; liquid/liquid separation; gas/liquid separation; solid/liquid separation; oil/water/gas separation; treatment and pumping; water treatment; heat exchange; and injection of water or gas into the well.

Further information on the current state of underwater hydrocarbon production facilities are available in the document OTC 24307 "STEPS TO THE SUBSEA FACTORY" by Rune Ramberg (Statoil), Simon RH Davies (Statoil), Hege Rognoe (Statoil), and Ole Oekland (Statoil).

While underwater hydrocarbon production facilities provide numerous advantages, the construction, maintenance and control of an underwater hydrocarbon production facility are beset by various problems that grow as the depth increases.

In particular, each process is performed by an apparatus, which comprises motors and/or valves and/or sensors for detecting the characteristic physical quantities of the process, and is configured to work in a body of water. Since a complex underwater facility comprises a plurality of apparatuses connected to each other, it is necessary to prevent the malfunctioning of one apparatus from compromising the integrity and/or reliability and/or operation of the entire underwater facility. This situation calls for using control systems comprising relatively highly reliable underwater control devices capable of operating effectively at depth and isolating the malfunctioning apparatus from the rest of the plant and/or parts of the control system.

There are substantially three known types of underwater control devices. The first type comprises a waterproof box defining a chamber at atmospheric pressure, and at least one electronic component housed in the chamber at atmospheric pressure. This solution allows using electronic components present on the market, but, as the depth increases, the thickness and weight of the container also increase, to the point of making this solution not very attractive from an economic viewpoint.

A second type comprises a waterproof box defining a chamber at atmospheric pressure, an electronic component housed in the chamber at atmospheric pressure, a further waterproof box containing the first waterproof box, and a fluid interposed between the first and the second box. Just like the first type of technical solution, solutions ascribable to the second type are not very attractive from an economic viewpoint.

A third type of underwater control devices such as those described in PCT Patent Application No. WO 2015/188882 and EP Patent No. 2,666,956 A1 comprises a box with a chamber containing a sealing, compensated dielectric liquid and at least one electronic component placed in the liquid. PCT Patent Application No. WO 2015/188882 discloses a rigid housing filled with a dielectric fluid; one electric component provided inside the rigid housing, which comprises pressure-volume means arranged to enable a volume change of the rigid housing.

EP Patent No. 2,666,956 A1 discloses a modular electric device located under water and operating under relatively high pressure in water environment at relatively large depths, in which electric and power electronic systems are protected against the mechanical effect of relatively high pressure, applicable to energizing induction motors driving rotating machinery. The modular electric system is placed under water in a watertight container, which is provided with electric bushings and comprising at least one electric system which comprises modular functional electrical elements placed in a protective insulating capsule. The electric system is located in a closed container filled with a dielectric non-compressible liquid of a pressure similar to the pressure surrounding the container from external side of the container. At least one of the protective capsules contains an insulating medium of a pressure significantly lower than the pressure in the container and is furnished with means and/or for transferring heat generated in modular functional electrical elements. This type of underwater control devices requires electronic components designed to work under pressure and a pressure compensation mechanism.

A further type of underwater control devices is disclosed by PCT Patent Application No. WO 2007/010179. This document discloses a module for underwater installation, which comprises a component and a waterproof covering applied to the component, to protect the component from the water, which may enter into the box.

SUMMARY

The advantage of the present disclosure is to provide an underwater control device configured to mitigate certain of the drawbacks of certain of the known art.

In accordance with the present disclosure, an underwater control device is provided for an underwater hydrocarbon production facility, the underwater control device comprising:
- an underwater box defining a housing chamber;
- an active electronic component with a switching and/or isolation function, housed in the housing chamber
- a polymer block in which the active electronic component is embedded, and which is housed in the housing chamber;
- electrical connectors extending through the underwater box and configured to connect the active electronic component to a network of a control system; and
- a sensor configured to detect water and connected to the active electronic component.

It should be appreciated that the polymer block disclosed herein enables protecting the active electronic component from direct contact with water in the event of seepage occurring inside the underwater box. In this way, the underwater control device is also able to operate in the event of malfunction of the electronic components connected to the underwater control device.

In various embodiments, the sensor is able to detect the presence of water inside the underwater box. In accordance with a further embodiment, the sensor is able to detect the presence of water in a further underwater box to which the underwater control device is mechanically coupled.

In particular, the polymer block is made of polyurethane or epoxy resin.

These materials are capable of providing adequate impermeability and malleability.

In particular, the polymer block has a hardness between 60 and 90 Shore A.

It has been found that the indicated hardness range allows protecting the active electronic component even in the presence of fluids at relatively very high pressures.

In particular, the underwater box is waterproof. However, the box does not have very high relative thicknesses and, as the underwater box is made from parts assembled together, it is not possible to guarantee perfect sealing over time.

In particular, the underwater box comprises a box-shaped body and a lid sealingly fixed to the box-shaped body. In particular, the box is made of a metal material and requires at least one assembly stage. Furthermore, the underwater box communicates with the outside through the electrical connectors.

In particular, the lid supports the polymer block. In this way, the block occupies a well-defined position in the housing chamber. Furthermore, the polymer block is arranged at a distance from the walls of the underwater box.

In particular, the lid defines a space at least partially filled by said polymer block, inside which the active electronic component is embedded.

In practice, the polymer material is liquefied and injected around the active electronic component. The space in the lid can be advantageously used as an injection mould.

In particular, the underwater control device comprises a further active electronic component with a signal control function, connected to the active electronic component and arranged inside the box-shaped body, and further electrical connectors connected to the further active electronic component. In this way, a single underwater box contains two active electronic components: one with the function of controlling the operating signals of the function module to which it is associated, the other, located inside the polymer block and more protected, configured to detect operating anomalies and, if necessary, disconnecting the data and power lines from the control node with which it is associated.

In particular, the housing chamber is filled with a dielectric liquid. In this way, the additional underwater control device also has a certain level of protection against water seepage.

In accordance with a variant of the present disclosure, the housing chamber is filled by the polymer block. In this case, the underwater box contains just the active electronic component with the switching and/or isolation function.

In accordance with another variant, the housing chamber is filled with a gas under pressure.

In accordance with one particular embodiment, the underwater control device comprises at least a further electrical connector configured to connect the underwater control device to a further underwater control device.

When the underwater box contains just the underwater control device, the need arises to interface the underwater control device with a further underwater control device with the function of monitoring the signals and controlling part of the plant.

In particular, the active electronic component comprises a printed circuit board and at least one electronic item mounted on the printed circuit board and protruding from the printed circuit board.

The protection provided by the polymer block is able to protect the board from water even in the case where the polymer block is subjected to relatively very high pressures.

The present disclosure also relates to a control system configured to control an underwater hydrocarbon production facility.

In accordance with the present disclosure, a control system is provided for controlling an underwater hydrocarbon production facility comprising a plurality of interconnected function modules, the control system comprising a distributed-node network connected to each of said function modules at the respective nodes, and a plurality of underwater control devices, each of which is configured as previously described and is located at a respective node configured to disconnect the respective function module from the network.

The system is therefore capable of disconnecting temporarily failing functional modules.

In particular, the system comprises an underwater master control device configured to disconnect a section of the network from the remainder of the network.

In particular, the system comprises at least two underwater master control devices configured to selectively disconnect respective sections of the network from the remainder of the network. In this way, it is possible to ensure operation of the plant even the event of one of the two control units failing.

Additional features and advantages are described in, and will be apparent from the following Detailed Description and the figures.

BRIEF DESCRIPTION OF DRAWINGS

Further characteristics and advantages of the present disclosure will become clear from the description that follows of various embodiments, with reference to the figures in the accompanying drawings, in which.

DETAILED DESCRIPTION

Figure 1:
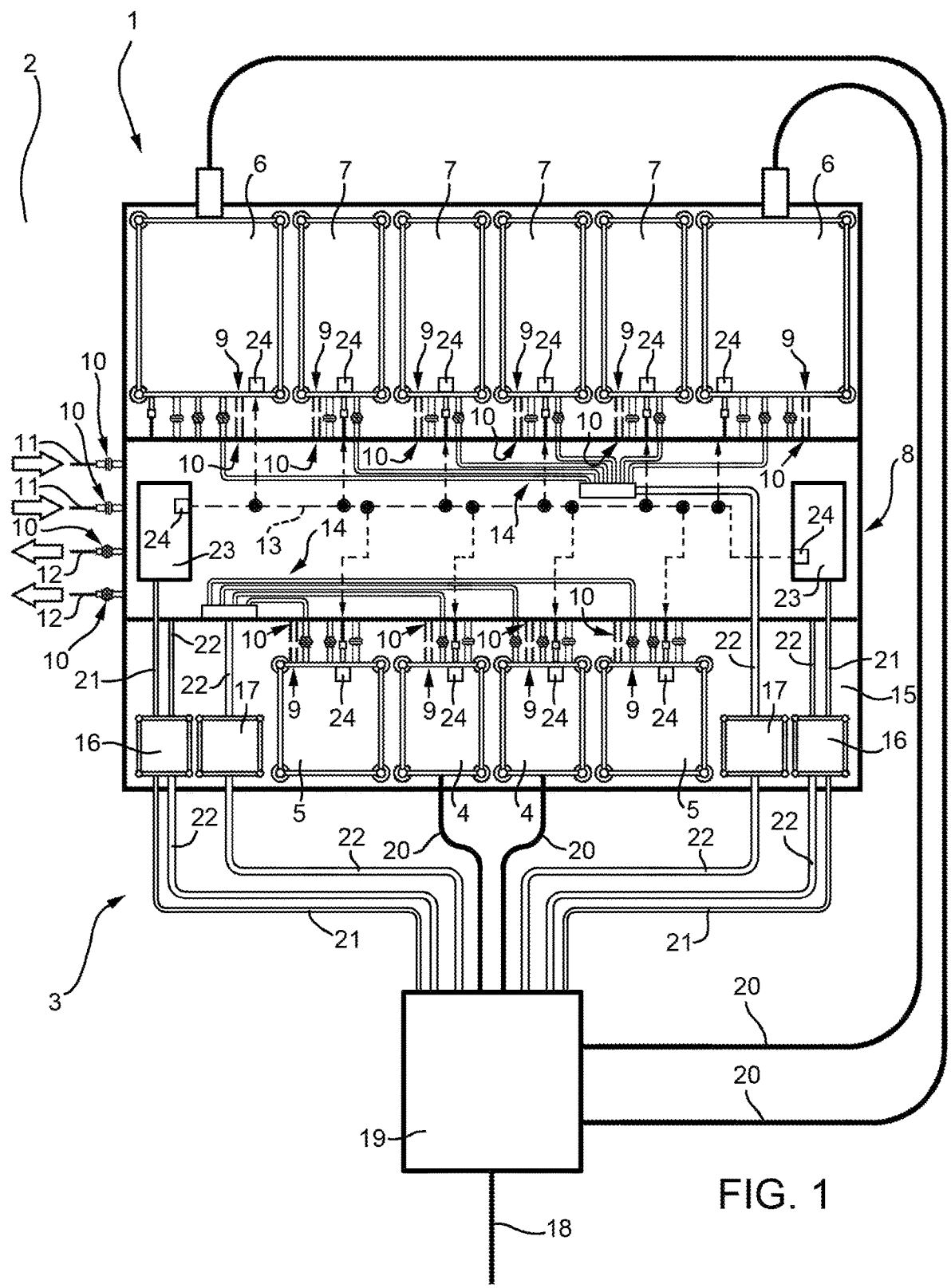
FIG. 1 is a schematic plan view, with parts removed for clarity, of an underwater hydrocarbon production facility according to a further embodiment of a submarine hydrocarbon production facility of the present disclosure.

Referring now to the example embodiments of the present disclosure illustrated in FIGS. 1 to 6, as seen in FIG. 1, reference numeral indicates an underwater hydrocarbon production facility. The plant 1 is arranged on a bed 2 of a body of water relatively near a subsea well or well field (not shown in the accompanying figures), and comprises a cluster 3, which comprises a plurality of function modules 4, 5, 6 and 7 configured to process hydrocarbons, and an interconnection unit 8 configured to be arranged on the bed 2 of the body of water to connect the function modules 4, 5, 6 and 7 to each other. Each of the function modules 4, 5, 6 and 7 comprises a plurality of connection elements 9, while the interconnection unit 8 comprises a plurality of connection elements 10, each configured for being operatively connected to a corresponding connection element 9 of one of the function modules 4, 5, 6 and 7.

In greater detail, each of the function modules 4, 5, 6 and 7 houses a respective apparatus configured to process hydrocarbons or perform operations related to hydrocarbon processing.

In this description, the term apparatus is used to indicate:
Multiphase pump (function: multiphase pumping);
Liquid pump;
Gas compression;
Liquid/liquid separator;
Gas/liquid separator;
Solid/water separator;
Heat exchanger;
Water injection pump;
Chemical injection pump;
Gas treatment device;
Oil treatment device;
Water treatment device.

The interconnection unit 8 comprises further connection elements 10 configured to connect the inlet pipes 11, and another two connection elements 10 configured to connect to two respective outlet pipes 12 that run to respective headers (not shown in the accompanying figures).

The connection elements 10 are interconnected by tubes (which are not shown in FIG. 1) housed in the interconnection unit 8, and configured to transfer process fluids between the function modules 4, 5, 6 and 7, the inlet pipes 11 and the outlet pipes 12, according to a certain layout.

The interconnection unit 8 also comprises valves (which are not shown in FIG. 1) housed inside the interconnection unit 8, and configured to regulate the flow of the process fluids.

The interconnection unit 8 is configured to collect and distribute signals, electric power, chemical products and hydraulic fluids to and from the function modules 4, 5, 6 and 7. In consequence, the interconnection unit 8 comprises a control bus 13 and a plurality of tubes 14 configured to convey chemical products and/or hydraulic fluids.

The plant comprises a platform 15 on which the interconnection unit 8 and the function modules 4, 5, 6 and 7 rest, two junction boxes 16, and two distribution units 17.

Signals, chemical products, hydraulic fluids and electric power are conveyed through an umbilical 18 to a switching unit 19, which distributes electric power directly through power cables 20 to the modules 4 and 6 that house pumps or compressors.

The switching unit 19 is connected to the two junction boxes 16 via a control bus 21 and a tube bundle 22 for hydraulic fluids, and to the chemical product distribution unit 17 by a tube bundle 22.

The junction boxes 16 and the chemical product distribution units 17 are in turn connected to the interconnection unit 8.

The interconnection unit 8 shown in FIG. 1 comprises two junction boxes 23, and two underwater control devices 24 that, in the case show, are associated with the respective junction boxes 23 and are configured to process signals acquired from the function modules 4, 5, 6 and 7, to emit control signals configured to control the function modules 4, 5, 6 and 7, and to open and close the valves (not shown in the accompanying figures).

Each of the function modules 4, 5, 6 and 7 comprises an underwater control device 24 configured to control the parameters related to the associated process.

In particular, each of the underwater control devices 24 of the interconnection unit 8 has the master function and is connected to all of the underwater control devices 24, which are installed in the function modules 4, 5, 6 and 7 and have the slave function.

The entire supervision of the plant 1 is carried out from a surface control station equipped with monitors (not shown in the accompanying figures).

In the case shown, the control system of the underwater plant 1 has a distributed-node architecture and comprises: a distributed-node network comprising the control buses 13 and 21, and the junction boxes 16 and 23. The network connects to the function modules 4, 5, 6 and 7, or rather the underwater control devices 24 associated with the respective function modules 4, 5, 6 and 7, and the switching unit 19 that, in turn, is connected to a surface control unit (not shown in the accompanying figures). Each underwater control device 24 is placed at a respective node of the network to isolate the respective function module 4 or 5 or 6 or 7 from the control network.

In the case shown, the underwater control devices 24 arranged in respective junction boxes 23 both have the master function and perform exactly the same functions, while the network connects the master control devices 24 to the switching unit 19 independently of one another. In consequence, the control system is redundant.

In accordance with a variant that is not shown, the master control devices 24 are placed at other points of the control network, but conveniently inside the interconnection unit 8.

Figure 2:
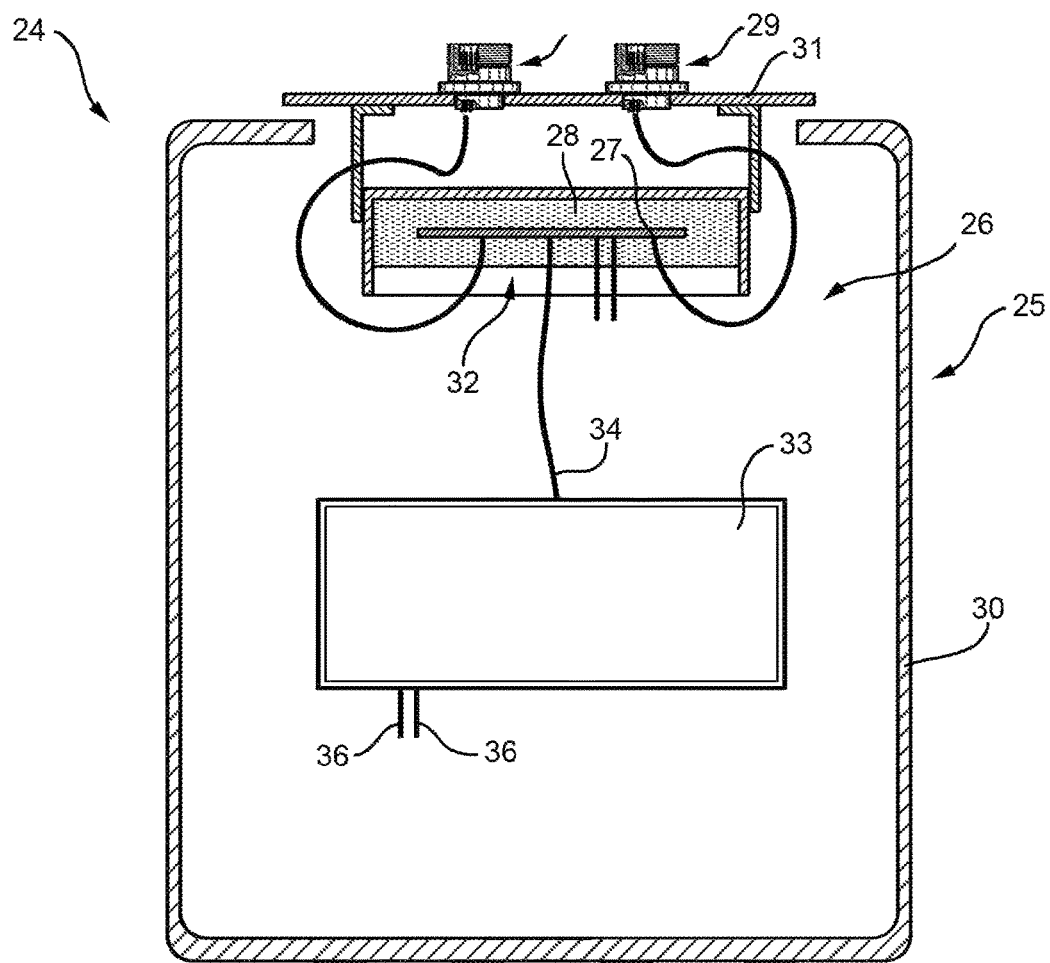
FIG. 2 is a section view, with parts removed for clarity, of a control device made according to a first embodiment of the present disclosure.

Referring to FIG. 2, the underwater control device 24 comprises: an underwater box 25 defining a housing chamber 26; an active electronic component 27, with a switching and/or isolation function, housed in the housing chamber 26; a polymer block 28, in which the active electronic component 27 is embedded, and which is housed in the housing chamber 26; and electrical connectors 29 extending through the underwater box 25 and configured to connect the active electronic component 27 to the network of the control system, in this case to the control bus 13 (FIG. 1).

The block 28 is made of polyurethane or epoxy resin. In particular, the block 28 has a hardness between 60 and 90 Shore A. In practice, the polymer material is formed around the active electronic component 27.

The underwater box 25 is a waterproof box and is made of a metal material.

The underwater box 25 comprises a box-shaped body 30 and a lid 31 sealingly fixed to the box-shaped body 30, such as by bolts or screws.

The lid 31 defines a space 32 at least partially occupied by the polymer block 28, inside which the active electronic component 27 with the switching and/or isolation function is embedded.

The underwater control device 24 comprises a electronic component 33 with a signal control function. The electronic component 33 is placed in the box-shaped body 30 and is connected to the active electronic component 27 with the switching and/or isolation function by cables 34 and to further electrical connectors 35 connected by cables 36. The electrical connectors 35 are connected to components, for example sensors and/or actuators, of one of the modules 4, 5, 6 or 7.

The housing chamber 26 is filled with a dielectric liquid.

In particular, the active electronic component 27 with the switching and/or isolation function comprises a printed circuit board embedded in the polymer block 28 and at least one electronic item (not shown) mounted on the board.

Similarly, the electronic component 33 comprises a printed circuit board and at least one electronic item (not shown) mounted on the board.

In accordance with a variant not shown in the accompanying figures, the electronic component 33 is placed inside a waterproof box, in turn placed inside the underwater box 25.

In short, the control device 24 in FIG. 2 comprises an underwater box 25 containing both an active electronic component 33 having the function of supervising the operation of the associated module 4, 5, 6 or 7, or of supervising a series of modules 4, 5, 6 and 7 when mounted in the junction box 23 (FIG. 1), and an active electronic component 27 capable of isolating a module 4, 5, 6 or 7, or an entire section of the network in the event of a malfunction being detected in a module 4, 5, 6 or 7, or in a section of the network.

Figure 3:
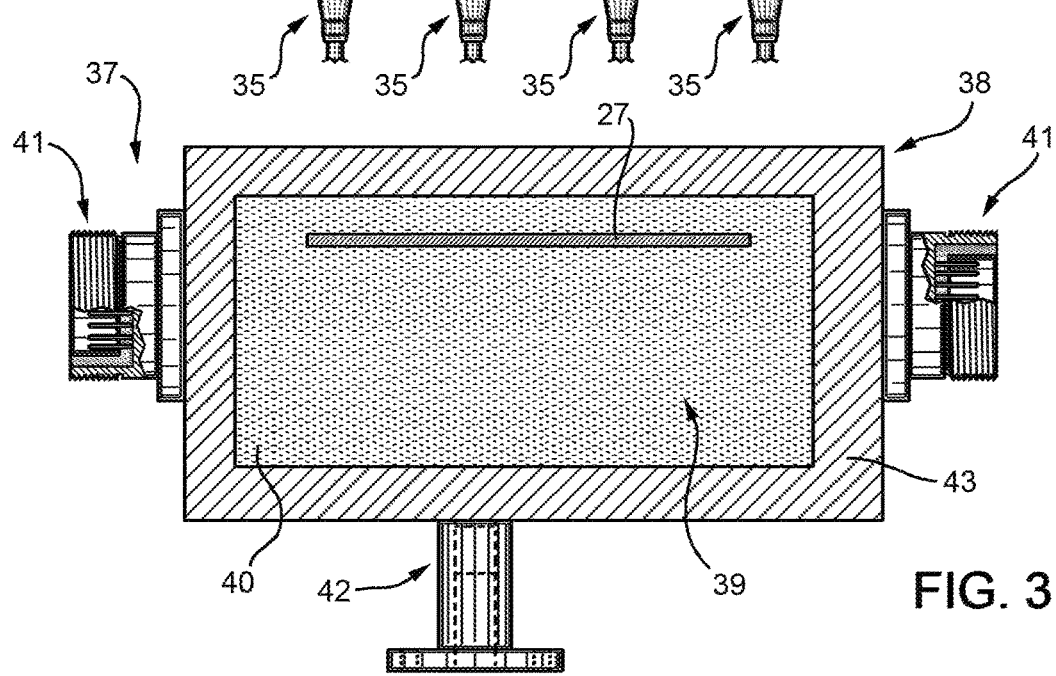
FIG. 3 is a section view, with parts removed for clarity, of a control device made according to a second embodiment of the present disclosure.

Referring to FIG. 3, reference numeral 37 indicates an underwater control device configured to isolate a section of network from the remainder of the network and to be coupled to a control device (not shown) configured to control the operation of a module 4, 5, 6 or 7, or supervise the operation of a series of modules 4, 5, 6 and 7. In other words, the underwater control device 37 has the sole function of detecting a malfunction and isolating a section of the network.

The underwater control device 37 comprises: an underwater box 38 defining a housing chamber 39; the active electronic component 27, with a switching and/or isolation function, housed in the housing chamber 39; a polymer block 40 in which the active electronic component 27 is embedded, and which is housed in the housing chamber 39; and electrical connectors 41 and 42 extending through the box 38 and configured to connect the active electronic component 27 to the network of the control system, in this case to the control bus 13 (FIG. 1).

The block 40 is made of polyurethane or epoxy resin, has a hardness between 60 and 90 Shore A, and occupies the entire housing chamber 39.

The underwater box 38 is a waterproof box made of a metal material and comprises a box-shaped body 43 and a lid, not shown, sealingly fixed to the box-shaped body 43, such as by bolts or screws.

The active electronic component 27 with the switching and/or isolation function is connected to the electrical connectors 41 and 42 by respective cables (not shown in the accompanying figures).

Figure 4:
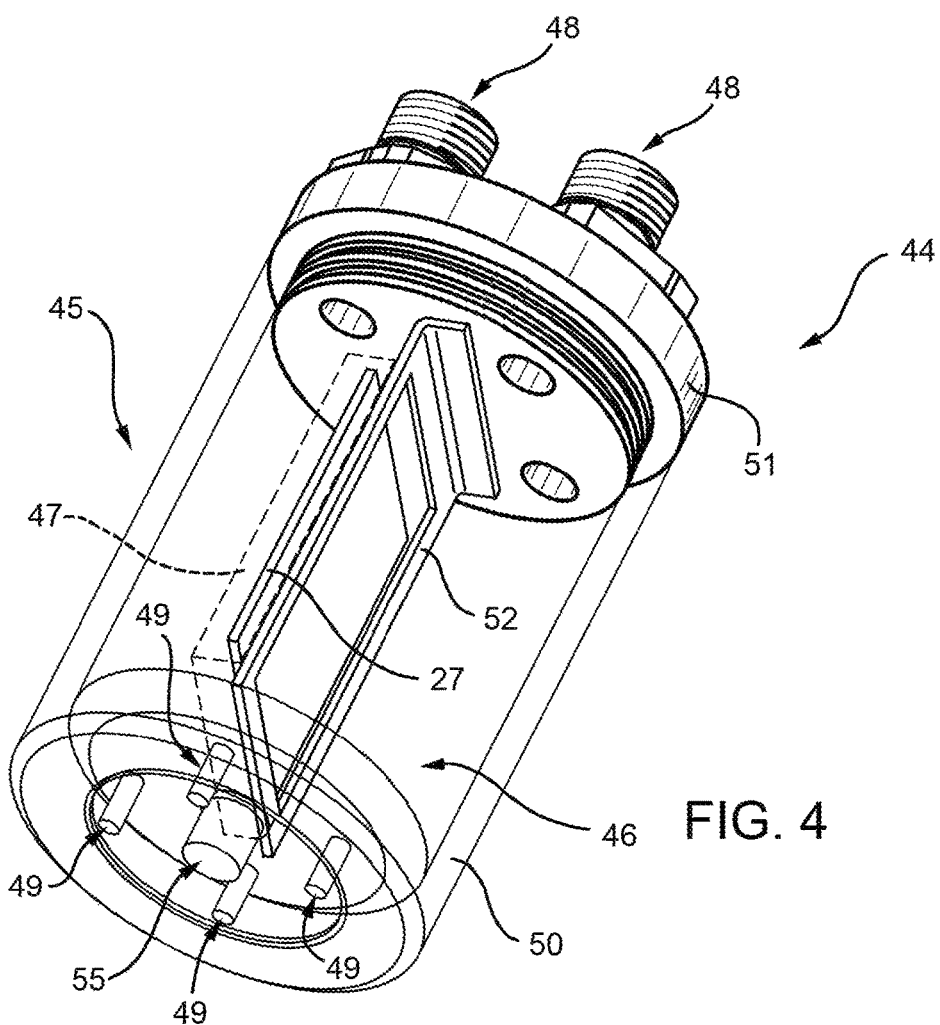
FIG. 4 is a perspective vista, with parts removed for clarity, of a control device made according to a third embodiment of the present disclosure.
Figure 5:
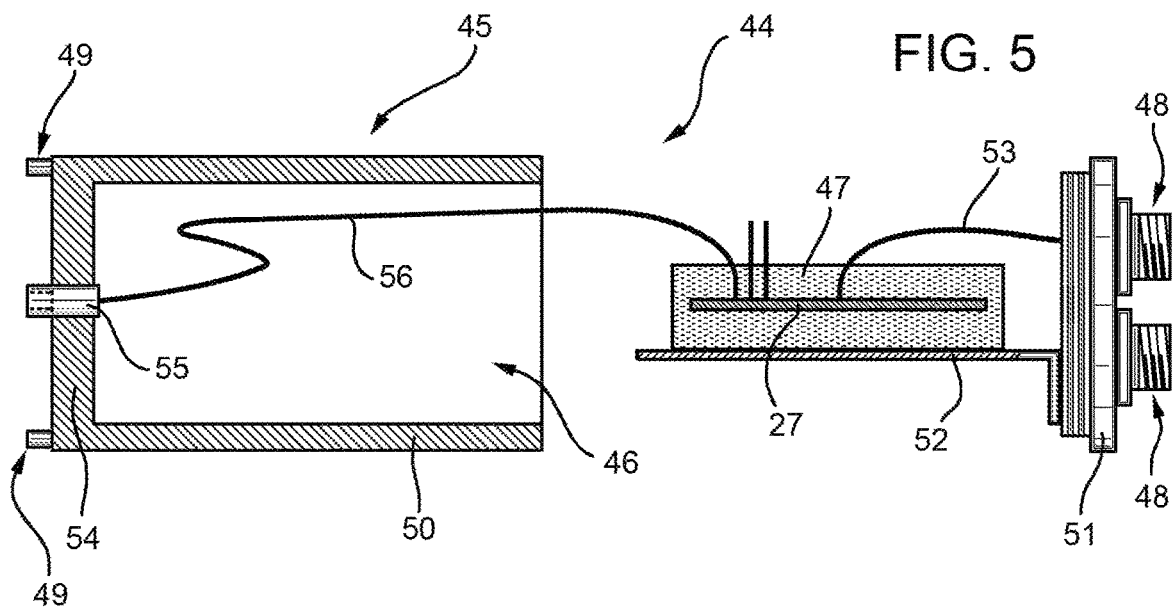
FIG. 5 is a section view, with parts removed for clarity and partially exploded, of the control device in FIG. 4.

Referring to FIGS. 4 and 5, reference numeral 44 indicates an underwater control device configured to isolate a section of network from the remainder of the network and for being coupled to a control device (not shown) configured to control the operation of a module 4, 5, 6 or 7, or supervise the operation of a series of modules 4, 5, 6 and 7. In other words, the underwater control device 44 has the sole function of detecting a malfunction and isolating a section of the network, in a similar manner to underwater control device 37.

The underwater control device 44 comprises: an underwater box 45 defining a housing chamber 46; an active electronic component 27, with a switching and/or isolation function, housed in the housing chamber 46; a polymer block 47 in which the active electronic component 27 is embedded, and which is housed in the housing chamber 46; and electrical connectors 48 and 49 extending through the box 45 and configured to connect the active electronic component 27 to the network of the control system, in this case to the control bus 13 (FIG. 1).

The block 47 is made of polyurethane or epoxy resin. In particular, the block 47 has a hardness between 60 and 90 Shore A. In practice, the polymer material is formed around the active electronic component 27.

The underwater box 45 is a waterproof box made of a metal material and comprises a cylindrical box-shaped body 50 and a lid 51 sealingly fixed to the box-shaped body 50, such as by screwing the lid 51 onto the box-shaped body.

The lid 51 supports a projecting bracket 52 arranged in the housing chamber 46 and configured to support the block 47 and the active electronic component 27. The lid 51 also supports the electrical connectors 48, which extend on the opposite side to the bracket 52 and are connected to the active electronic component 27 by cables 53 (FIG. 5).

The box-shaped body 50 comprises a bottom wall 54 along which the electrical connectors 49 extend and a sensor 55 configured to detect the presence of water and connected to the active electronic component 27 by a cable 56 (FIG. 5).

In particular, the housing chamber 46 is filled with a gas. In particular, the gas is air at atmospheric pressure or slightly in overpressure.

Figure 6:
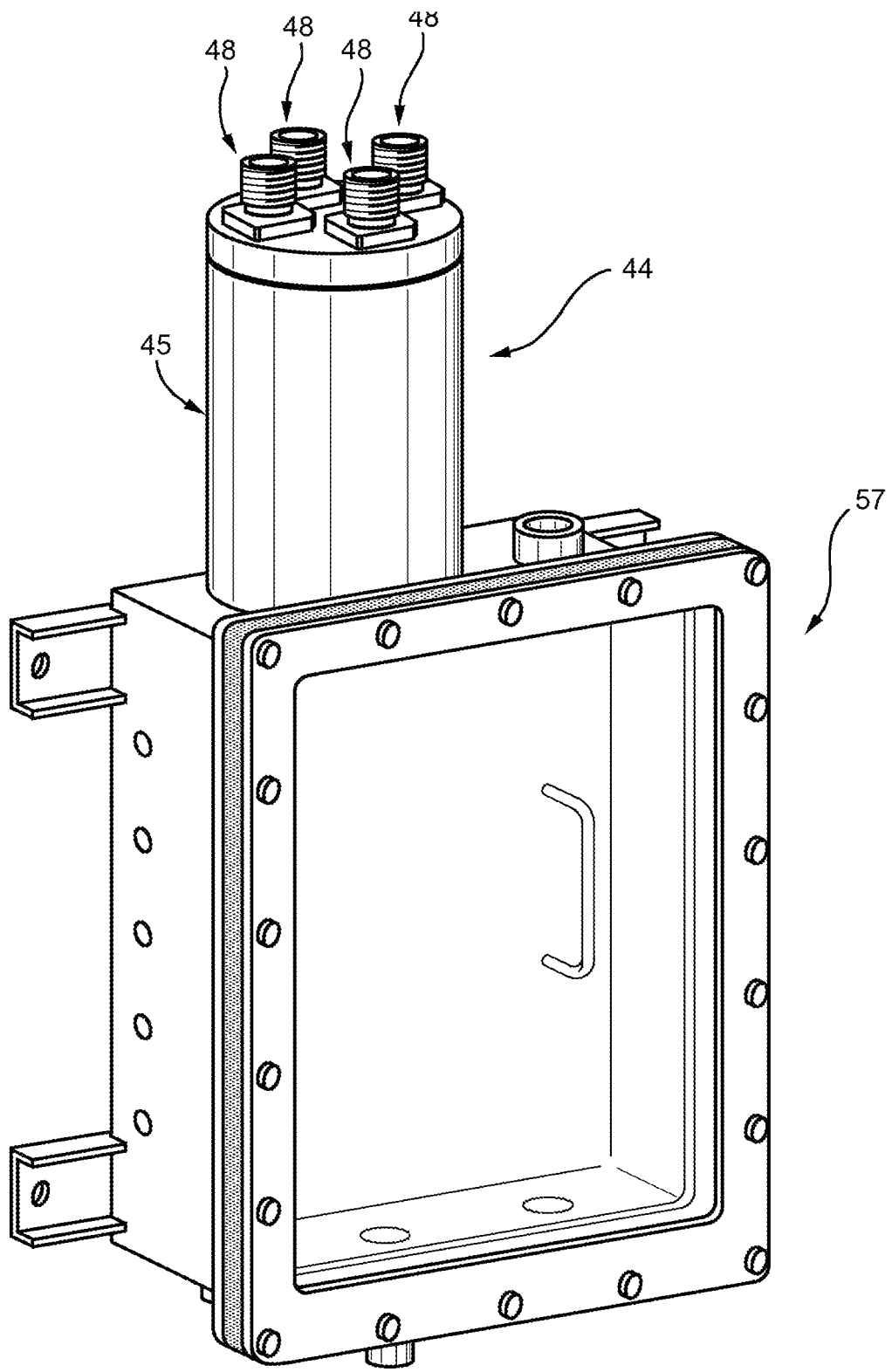
FIG. 6 is a perspective vista, with parts removed for clarity, of the control device in FIG. 4 inserted in a control system.

In particular, referring to FIG. 6, the bottom wall 54 is configured to be connected directly to an underwater control device 57 that performs the control and management functions of one of the modules 4, 5, 6 or 7. Underwater control device 44 is connected to underwater control device 57 structurally and hermetically by the bottom wall 54 and functionally by connectors 49 (FIG. 5).

Finally, it should be appreciated that variants regarding the present disclosure can be implemented with respect to the embodiments described with reference to the accompanying drawings without departing from the scope of the claims. For example, although only shown in the embodiment in FIGS. 4 and 5, it should be appreciated that the other embodiments can also comprise a water-detection sensor connected to the active electronic component. Accordingly, various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An underwater hydrocarbon production facility underwater control device comprising:
an underwater box defining a housing chamber;
an active electronic component housed in the housing chamber, the active electronic component having one of a switching and an isolation function;
a polymer block housed in the housing chamber, wherein the active electronic component is embedded in the polymer block;
an electrical connector extending through the underwater box and configured to connect the active electronic component to a network of a control system; and
a sensor configured to detect water and connected to the active electronic component.

2. The underwater hydrocarbon production facility underwater control device of claim 1, wherein the polymer block is made of a material selected from the group consisting of: a polyurethane and an epoxy resin.

3. The underwater hydrocarbon production facility underwater control device of claim 1, wherein the polymer block features a hardness between 60 and 90 Shore A.

4. The underwater hydrocarbon production facility underwater control device of claim 1, wherein the underwater box is waterproof.

5. The underwater hydrocarbon production facility underwater control device of claim 1, wherein the underwater box comprises a box-shaped body and a lid sealingly fixed to the box-shaped body.

6. The underwater hydrocarbon production facility underwater control device of claim 1, wherein the housing chamber is configured to be filled with a dielectric liquid.

7. The underwater hydrocarbon production facility underwater control device of claim 1, wherein the housing chamber is configured to be filled with a gas under pressure.

8. The underwater hydrocarbon production facility underwater control device of claim 1, further comprising at least a further electrical connector configured to be connected to a further underwater hydrocarbon production facility underwater control device.

9. The underwater hydrocarbon production facility underwater control device of claim 1, wherein said active electronic component comprises a printed circuit board and at least one electronic item mounted on the printed circuit board and protruding from the printed circuit board.

10. An underwater hydrocarbon production facility control system comprising:
a distributed-node network connected to each of a plurality of interconnected function modules at a respective node of the distributed-node network; and
a plurality of underwater control devices, wherein for each of the function modules, one of the underwater control devices is located at the respective node of that function module and is configured to selectively disconnect that function module from the distributed-node network, and wherein each of the underwater control devices comprises:
an underwater box defining a housing chamber;
an active electronic component housed in the housing chamber, the active electronic component having one of a switching and an isolation function;
a polymer block housed in the housing chamber, wherein the active electronic component is embedded in the polymer block;
an electrical connector extending through the underwater box and configured to connect the active electronic component to a network of a control system; and
a sensor configured to detect water and connected to the active electronic component.

11. The underwater hydrocarbon production facility control system of claim 10, further comprising an underwater master control device configured to disconnect a section of the distributed-node network from a remainder of the distributed-node network.

12. The underwater hydrocarbon production facility control system of claim 10, further comprising at least two underwater master control devices, each configured to disconnect a respective section of the distributed-node network from a remainder of the distributed-node network.

13. An underwater hydrocarbon production facility underwater control device comprising:
an underwater box defining a housing chamber and comprising a box-shaped body and a lid sealingly fixed to the box-shaped body;
an active electronic component housed in the housing chamber, the active electronic component having one of a switching and an isolation function;
a polymer block housed in the housing chamber, wherein the active electronic component is embedded in the polymer block and the lid of the underwater box supports the polymer block;
an electrical connector extending through the underwater box and configured to connect the active electronic component to a network of a control system; and
a sensor configured to detect water and connected to the active electronic component.

14. The underwater hydrocarbon production facility underwater control device of claim 13, wherein the lid defines a space at least partially filled by said polymer block in which the active electronic component is embedded.

15. The underwater hydrocarbon production facility underwater control device of claim 13, further comprising a further active electronic component with a signal control function, the further active electronic component being connected to a further electrical connector and to the active electronic component and arranged inside the box-shaped body.

16. An underwater hydrocarbon production facility underwater control device comprising:
an underwater box defining a housing chamber;
an active electronic component housed in the housing chamber, the active electronic component having one of a switching and an isolation function;
a polymer block which fills the housing chamber, wherein the active electronic component is embedded in the polymer block;
an electrical connector extending through the underwater box and configured to connect the active electronic component to a network of a control system; and a sensor configured to detect water and connected to the active electronic component.

\* \* \* \* \*